United States Patent
Huh

(10) Patent No.: US 8,959,662 B2
(45) Date of Patent: Feb. 24, 2015

(54) GRINDING MODE SELECTOR SWITCH FOR WELDING MASKS

(71) Applicant: Otos Tech Co., Ltd., Seoul (KR)

(72) Inventor: Moon Young Huh, Seoul (KR)

(73) Assignee: Otos Wing Co., Ltd. (KR)

( * ) Notice: Subject to any disclaimer, the term of this patent is extended or adjusted under 35 U.S.C. 154(b) by 123 days.

(21) Appl. No.: 13/908,186

(22) Filed: Jun. 3, 2013

(65) Prior Publication Data

US 2013/0340141 A1    Dec. 26, 2013

(30) Foreign Application Priority Data

Jun. 21, 2012  (KR) .......................... 10-2012-0066951

(51) Int. Cl.
*A61F 9/06*    (2006.01)

(52) U.S. Cl.
CPC ....................................... *A61F 9/067* (2013.01)
USPC ............ 2/8.2; 2/8.3; 2/8.4; 2/8.5; 2/8.7; 2/8.8

(58) Field of Classification Search
CPC ........... A61F 9/06; A61F 9/064; A61F 9/065; A61F 9/067; A61F 9/061; A61F 9/062
USPC .................. 2/410, 8.2–8.5, 8.1, 7, 8.7, 8.8; 307/122, 139, 141, 142; 359/601, 314
See application file for complete search history.

(56) References Cited

U.S. PATENT DOCUMENTS

| | | | | |
|---|---|---|---|---|
| 4,567,377 A | * | 1/1986 | Amlani et al. | 307/112 |
| 4,863,244 A | * | 9/1989 | Fuerthbauer et al. | 349/14 |
| 6,070,264 A | * | 6/2000 | Hamilton et al. | 2/8.8 |
| 6,472,619 B1 | * | 10/2002 | Halphide | 200/43.16 |
| 7,934,846 B1 | * | 5/2011 | Schwanz | 362/106 |
| 8,042,958 B2 | * | 10/2011 | Sundell | 359/614 |
| 8,860,257 B2 | * | 10/2014 | Schiefermuller et al. | 307/122 |
| 2006/0285330 A1 | * | 12/2006 | Sundell | 362/293 |
| 2009/0094721 A1 | * | 4/2009 | Becker | 2/8.8 |
| 2010/0053541 A1 | * | 3/2010 | Sundell | 351/44 |
| 2011/0316516 A1 | * | 12/2011 | Schiefermuller et al. | 323/318 |
| 2013/0340141 A1 | * | 12/2013 | Huh | 2/8.8 |
| 2014/0013479 A1 | * | 1/2014 | Magnusson et al. | 2/8.7 |

FOREIGN PATENT DOCUMENTS

KR    1020110007023    1/2011

* cited by examiner

*Primary Examiner* — Gloria Hale
(74) *Attorney, Agent, or Firm* — Cantor Colburn LLP

(57) ABSTRACT

A grinding mode selector switch for welding masks which controls an anti-glare device blocking hazardous light during a welding operation or an operation using a cutting torch and protecting eyes of a worker during a grinding operation without taking off a welding mask during the welding operation and the grinding operation is disclosed. The grinding mode selector switch for welding masks is installed on the outer surface of the welding mask and is not touched by an external object, and the protruding height of a button protective cap is equal to or greater than the height of a button so as to prevent the button from being touched by an external object when the worker performs an operation.

5 Claims, 9 Drawing Sheets

GRINDING MODE SELECTOR SWITCH FOR WELDING MASKS

BACKGROUND OF THE INVENTION

1. Field of the Invention

The present invention relates to a grinding mode selector switch for welding masks which selectively controls a welding operation and a grinding operation, and more particularly to a grinding mode selector switch for welding masks which stably protects eyes of a worker, easily achieves mode switching without taking off a welding mask (a welding helmet or a protective mask), is provided with a button which does not protrude to outside, and is thus safe to use so as not to generate unintentional malfunction due to operation environments.

2. Description of the Related Art

FIG. 1 is a perspective view illustrating a protective mask provided with a conventional anti-glare device. As exemplarily shown in FIG. 1, a protective mask 1, the front surface of which is provided with a conventional anti-glare device 2, reduces illumination of light applied to eyes of a worker through an anti-glare plate 5, i.e., a liquid crystal display (LCD), of the anti-glare device 2.

That is, optical sensors 4, such as photodiodes, provided on the front surface of the anti-glare device 2 senses light generated by a welding or cutting torch, and a control circuit installed in the anti-glare device 2 decreases brightness of the LCD so as to reduce illumination of light passing through the anti-glare plate 5, thus protecting eyes of a worker wearing the protective mask 1.

However, in case of the conventional anti-glare device 2 mounted on the welding mask, a user needs to directly manipulate control switches, which control power on/off, adjust concentration of shutter liquid crystals, adjust sensitivity of the optical sensors 4, and control time delay, or a variable volume switch by hand, and manipulation to switch the welding mask from a welding operation to a grinding operation is inconvenient.

In order to switch the welding mask from the welding operation to the grinding operation, the user needs to take off the above-described welding mask.

Therefore, the applicant of the invention, in Korean Patent Application No. 2009-0064277, discloses an anti-glare device selectively controlling a welding operation and a grinding operation. Here, in order to easily switch from a welding mode to a grinding mode, the anti-glare device is installed on the outer surface of a welding mask so as to switch the welding mask from the welding mode to the grinding mode.

However, if a worker performs the welding operation or the grinding operation in a narrow space, the switch may be touched by an external object (a protruding object around the switch) during the operation, and thus malfunction of the switch, i.e., switching of the welding mask to the grinding mode during the welding operation, may occur.

SUMMARY OF THE INVENTION

Therefore, the present invention has been made in view of the above problems, and it is an object of the present invention to provide a grinding mode selector switch for welding masks which may control a welding mask without taking off the welding mask if the welding mask is switched from a welding operation to a grinding operation or vice versa and prevent an external object from pressing a button or directly touching the button so as not to cause malfunction regardless of intention of a worker.

It is another object of the present invention to provide a grinding mode selector switch for welding masks which may be recognized by a worker wearing gloves.

In accordance with an aspect of the present invention, the above and other objects can be accomplished by the provision of a grinding mode selector switch for welding masks installed on the outer surface of a welding mask and controlling an anti-glare device protecting eyes of a worker during a welding operation and a grinding operation without taking off the welding mask during the welding operation and the grinding operation, wherein the protruding height of a button protective cap is equal to or greater than the height of a button so as to prevent the button from being touched by an external object regardless of intention of the worker.

A plurality of protrusions may be formed on a frame surface of the button protective cap so that the worker may recognize the grinding mode selector switch for welding masks by hand when wearing gloves or when bare handed.

BRIEF DESCRIPTION OF THE DRAWINGS

The above and other objects, features and other advantages of the present invention will be more clearly understood from the following detailed description taken in conjunction with the accompanying drawings, in which.

DETAILED DESCRIPTION OF THE INVENTION

Figure 1:
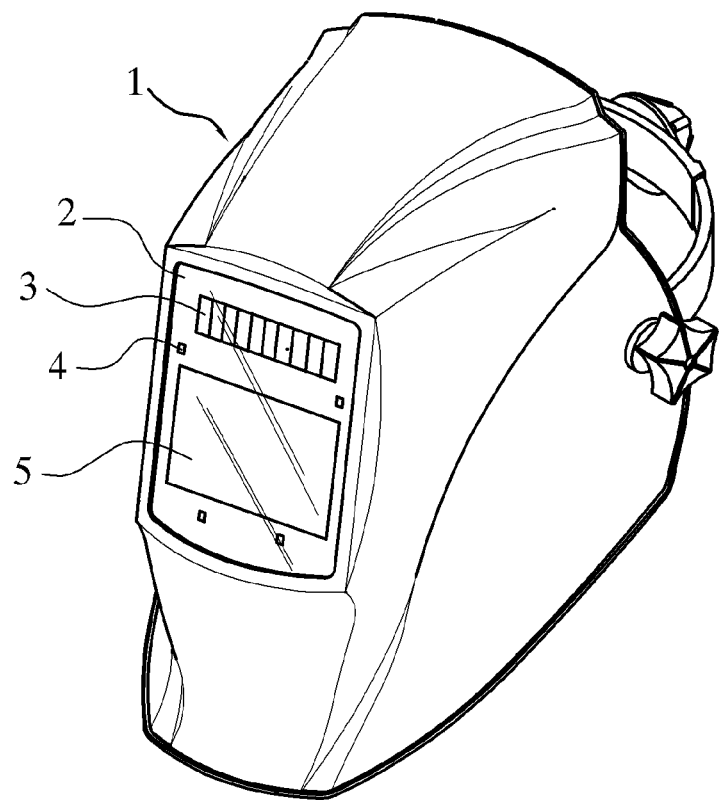
FIG. 1 is a perspective view illustrating a welding mask provided with a conventional anti-glare device.

Now, preferred embodiments in accordance with the present invention will be described in detail with reference to the annexed drawings.

A grinding mode selector switch 190 for welding masks in accordance with the present invention, as exemplarily shown in FIGS. 2 to 9, is mounted on the outer surface of a welding mask in which an anti-glare device 210 is installed. In the grinding mode selector switch 190 for welding masks, the height of a frame surface 110 of a button protective cap 100 is equal to or greater than the height of the surface of a button 150 so that the grinding mode selector switch 190 is not operated by an external object.

Figure 7:
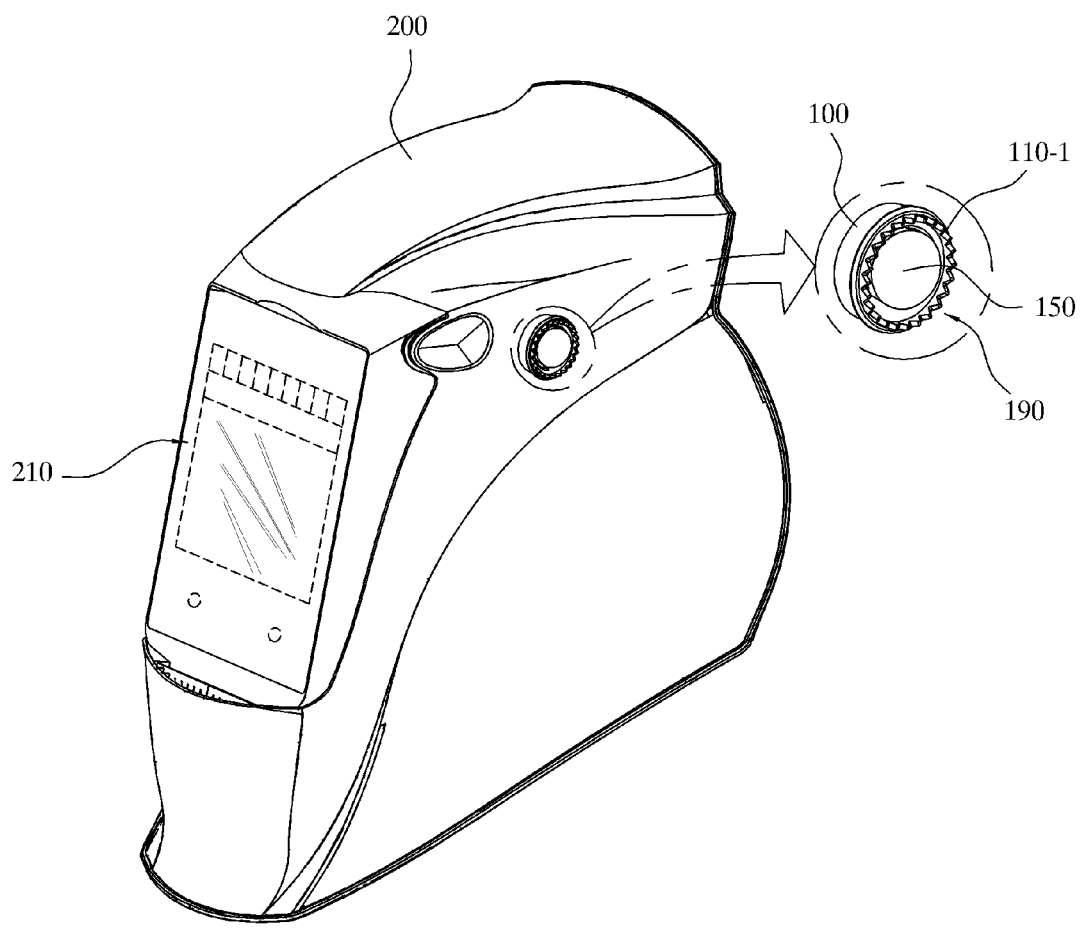
FIG. 7 is a partial enlarged view of the grinding mode selector switch for welding masks in accordance with the embodiment of the present invention shown in FIG. 6 mounted on the welding mask.

In the grinding mode selector switch 190 for welding masks in accordance with the present invention, a plurality of protrusions 110-1 is formed on the frame surface 110 of the button protective cap 100, as shown in FIG. 7, so that a worker may recognize the grinding mode selector switch 190 for welding masks by hand when wearing gloves or when bare handed.

Figure 2:
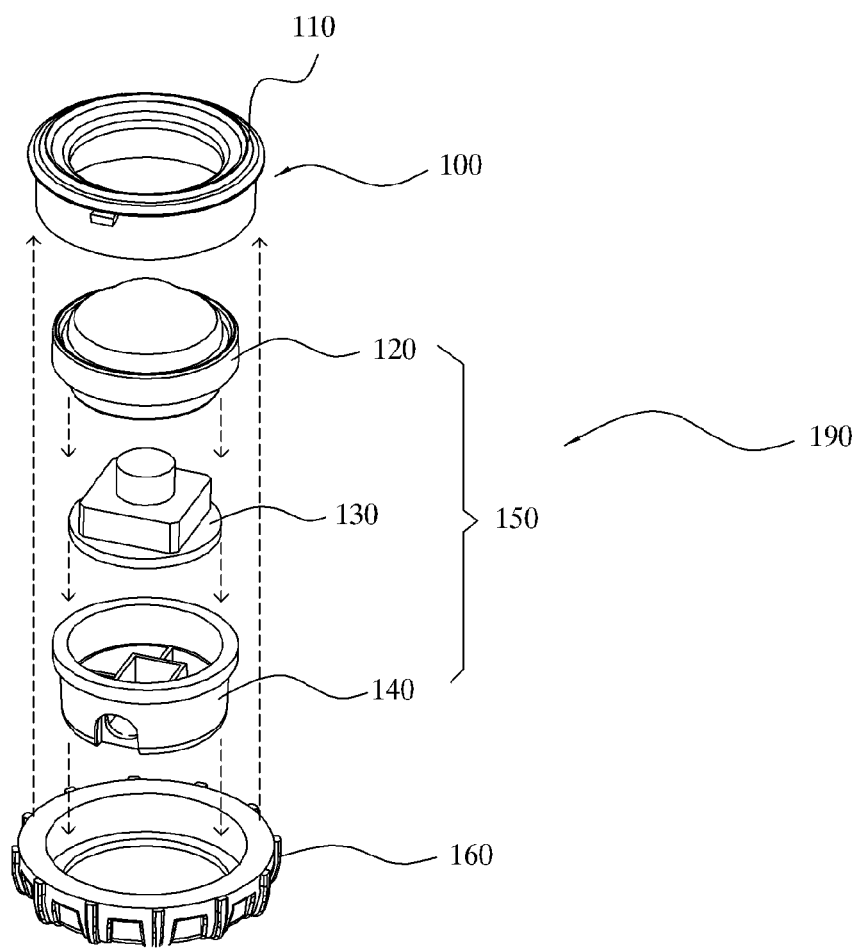
FIG. 2 is an exploded perspective view of a grinding mode selector switch for welding masks in accordance with one embodiment of the present invention.
Figure 3:
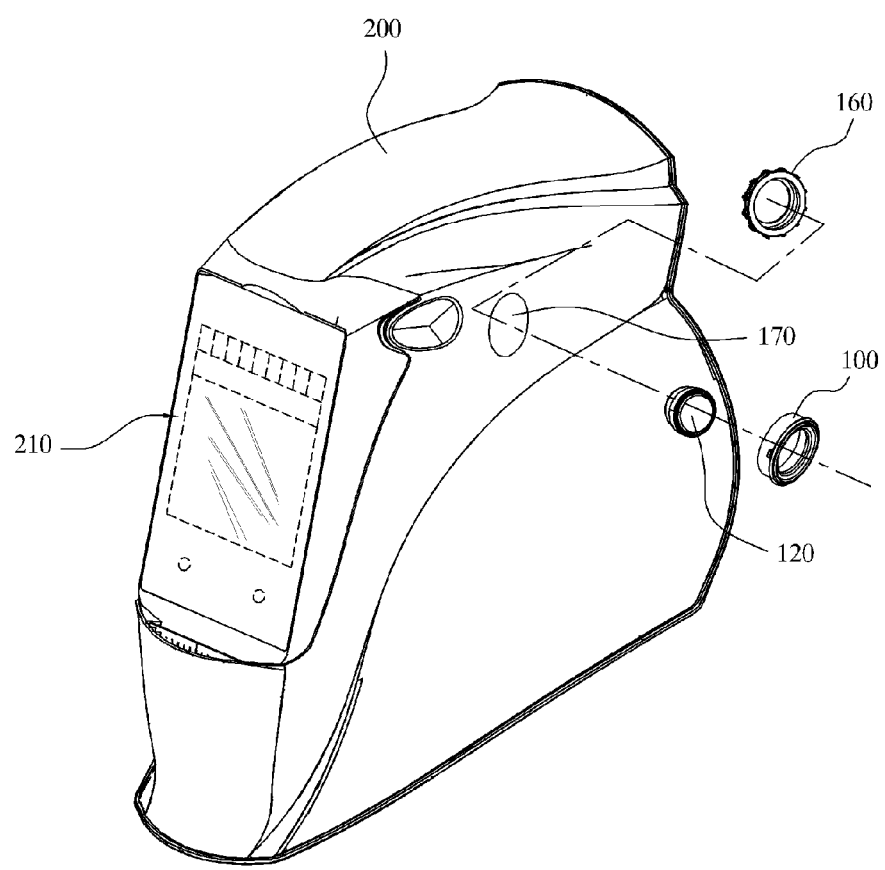
FIG. 3 is a view illustrating a state in which the grinding mode selector switch for welding masks in accordance with the embodiment of the present invention is mounted on a welding mask.
Figure 4:
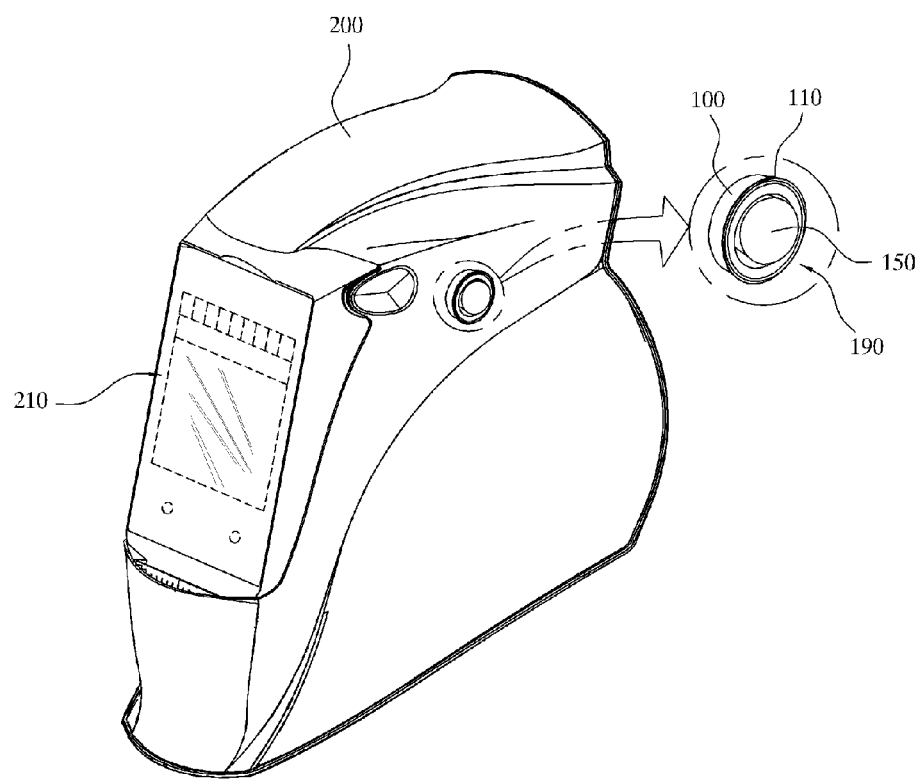
FIG. 4 is a partial enlarged view of the grinding mode selector switch for welding masks in accordance with the embodiment of the present invention mounted on the welding mask.

The grinding mode selector switch 190 for welding masks shown in FIG. 2 includes the button 150 including a PCB (printed circuit board) now written as "PCB" throughout the specification 130 and upper and lower cases 120 and 140 located above and below the PCB 130, the button protective cap 100 provided with the frame surface 110 to fix and protect the button 150, and a nut 160 combined with the button protective cap 100. The grinding mode selector switch 190 for welding masks protrudes from the side surface of the welding mask so as to achieve convenient switching between a welding operation and a grinding operation.

The button 150 may not protrude from the frame surface 110 of the button protective cap 100 so as not to be pressed by an external object.

Therefore, in the grinding mode selector switch for welding masks in accordance with the present invention which is installed on the outer surface of a welding mask and controls the anti-glare device 210 without taking off the welding mask to conveniently select an operation if the welding mask is switched between the welding operation and the grinding operation, the height of the protruding frame surface 110 of the button protective cap 100 is equal to or greater than the height of the surface of the button 150 so as to prevent the button 150 from being touched by an external object regardless of intention of a worker when the worker performs the operation.

Figure 5:
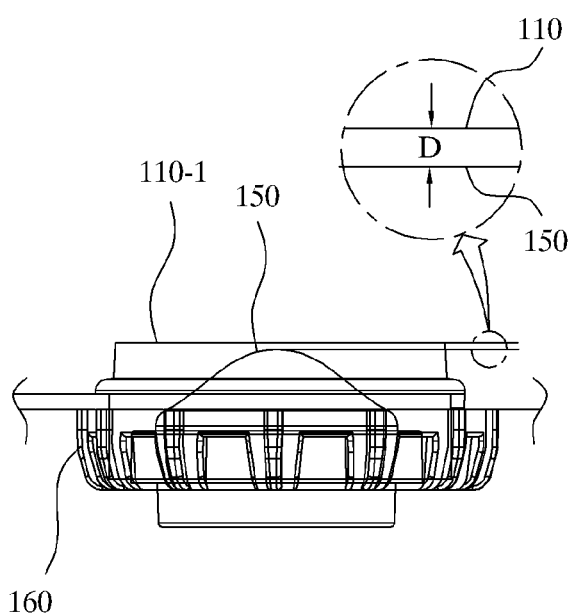
FIG. 5 is an enlarged view illustrating a height difference between a frame surface of a button protective cap and a button surface of the grinding mode selector switch for welding masks in accordance with the embodiment of the present invention.

If a worker controls the anti-glare device 210 mounted on the front surface of the welding mask shown in FIG. 5 to automatically block hazardous light during the welding operation and to prevent inability to see during the grinding operation, the worker needs to take off or lift up the welding mask to directly operate the anti-glare device 210. In order to solve such a problem, the grinding mode selector switch 190 for welding masks is installed on the outer surface of the welding mask. However, the button 150 may be pressed or be touched by an external object, thus causing unintentional operation. Therefore, in the present invention, in order to prevent pressing or touch of the button 150 of the grinding mode selector switch 190 for welding masks by the external object, the button protective cap 100 is provided.

The button protective cap 100 is configured such that the height of the frame surface 110 of the button protective cap 10 is equal to or greater than the height of the button 150 so that the button 150 does not protrude to the outside.

Figure 6:
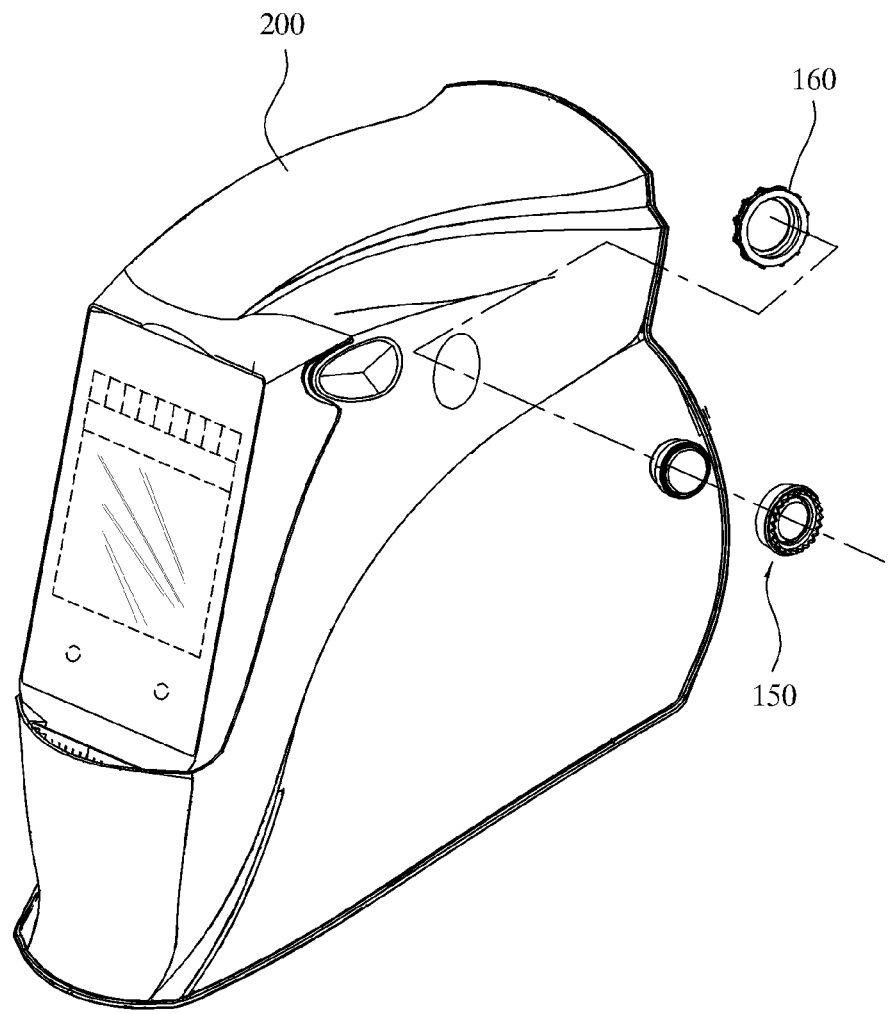
FIG. 6 is a view illustrating a state in which a grinding mode selector switch for welding masks in accordance with another embodiment of the present invention is mounted on a welding mask.
Figure 8:
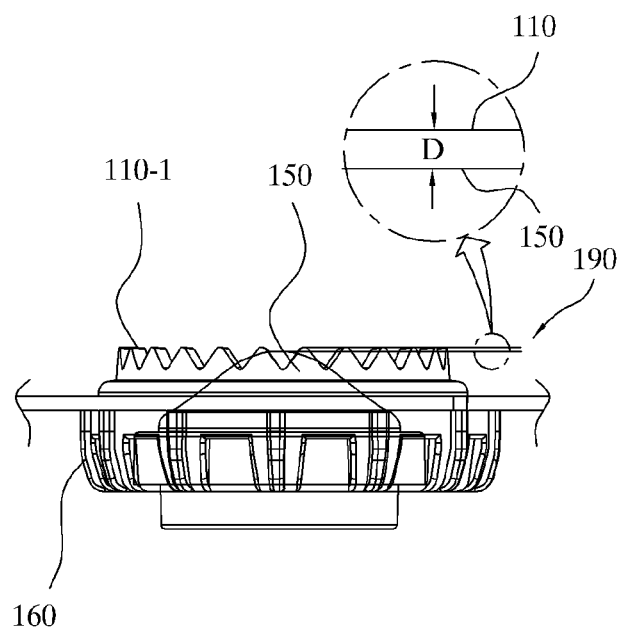
FIG. 8 is an enlarged view illustrating a height difference between a frame surface of a button protective cap and a button surface of the grinding mode selector switch for welding masks in accordance with the embodiment of the present invention.

In a grinding mode selector switch 190 for welding masks in accordance with another embodiment of the present invention, as shown in FIGS. 6 to 8, in order to solve misrecognition of the grinding mode selector switch 190 for welding masks by a worker wearing gloves due to inhibited tactile senses, a plurality of protrusions 110-1 is formed on a frame surface 110 of a button protective cap 100 so that the worker may easily recognize the grinding mode selector switch 190 for welding masks.

The protrusions 110-1 may be formed in a prism structure, such as a pointed mountain-shaped structure, a square pillar structure, a semicircular cylinder structure, etc., so that the worker may easily recognize the grinding mode selector switch 190 for welding masks.

Figure 9:
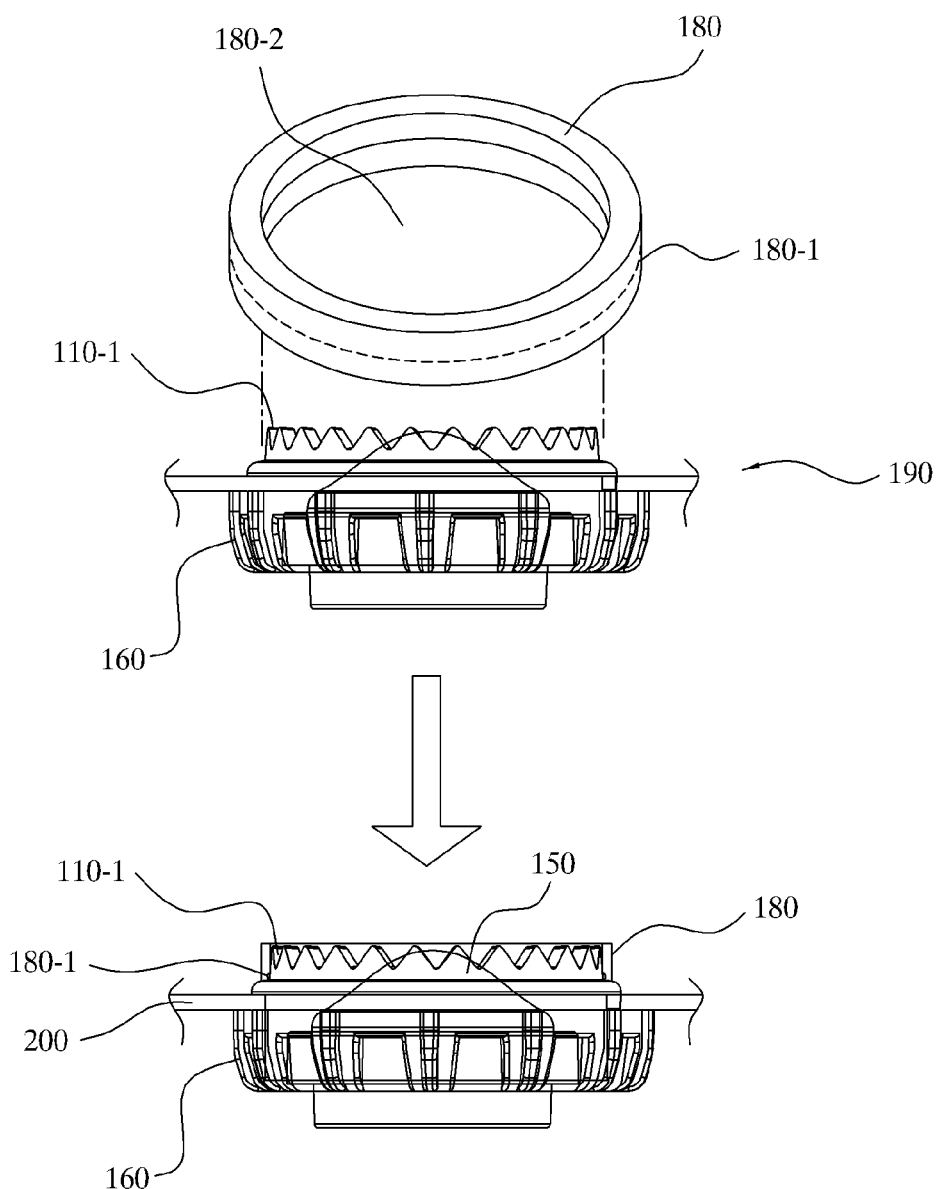
FIG. 9 is a view illustrating a state in which a sub-button protective cap is mounted on a button protective cap of a grinding mode selector switch for welding masks in accordance with yet another embodiment of the present invention.

A grinding mode selector switch 190 for welding masks in accordance with yet another embodiment of the present invention, as shown in FIG. 9, further includes a sub-button protective cap 180 including a through hole 180-2 formed at the center thereof so as to be detachably attached to the upper portion of a button protective cap 100 at need and a joining projection 180-1 formed on the side surface thereof.

If a worker does not desire to form protrusions 110-1 on the frame surface of the button protective cap 100, the worker may cover the button protective cap 100 with the sub-button protective cap 180.

In order to prevent the protrusions 110-1 formed on the frame surface of the button protective cap 100 from damaging the worker or worker's clothes when the worker touches the grinding mode selector switch 190 for welding masks with bare hands, the sub-button protective cap 180 may be attached to the button protective cap 100. Further, the sub-button protective cap 180 may be formed of a transparent material so that the protrusions 110-1 under the sub-button protective cap 180 are visible. The joining projection 180-1 is formed on the side surface of the sub-button protective cap 180 so as to combine the sub-button protective cap 180 and the button protective cap 100 with each other through the joining projection 180-1.

The position of the grinding mode selector switch 190 for welding masks in accordance with this embodiment of the present invention may be conveniently recognized from the outside by applying or attaching a fluorescent material to the button protective cap 100 or the button 150.

As described above, the grinding mode selector switch for welding masks in accordance with the present invention is installed on the outer surface of a welding mask and conveniently selects one operation without taking off the welding mask during the welding operation and the grinding operation.

Further, the welding mask (a welding helmet or a protective mask) includes an anti-glare device including an anti-glare plate formed on the front surface of the welding mask so that the grinding mode selector switch for welding masks in accordance with the present invention selectively controlling a welding operation or an operation using a cutting torch is not operated by touch of an external object. Therefore, the grinding mode selector switch for welding masks may prevent safety accidents.

As apparent from the above description, the present invention provides a grinding mode selector switch for welding masks which, if a welding operation is switched to a grinding operation, continuously performs these operations without taking off a welding mask, and is provided with a button protective frame so as to prevent abnormal operation of the grinding mode selector switch by an external object in a narrow space.

Further, the grinding mode selector switch for welding masks in accordance with the present invention includes a plurality of protrusions formed on a frame surface of a button protective cap so that a worker may easily recognize the grinding mode selector switch for welding marks by hand when wearing gloves or when bare handed so as to conveniently select an operation mode.

Although the preferred embodiments of the present invention have been disclosed for illustrative purposes, those skilled in the art will appreciate that various modifications, additions and substitutions are possible, without departing from the scope and spirit of the invention as disclosed in the accompanying claims.

What is claimed is:

1. A grinding mode selector switch for welding masks controlling an anti-glare device without taking off a welding mask during a welding operation and a grinding operation, comprising:
   a button having a printed circuit board (PCB) installed thereon;
   a button protective cap having a frame surface to fix and protect the button;
   a nut combined with the button protective cap so that the grinding mode selector switch protrudes from a side surface of the welding mask,
   wherein the button protective cap has a protruding height equal to or greater than a height of the button so as to prevent the button from being touched by an external object when a worker performs an operation.

2. The grinding mode selector switch for welding masks according to claim 1, wherein the button protective cap has an outer surface of a circular structure or a polygonal structure.

3. The grinding mode selector switch for welding masks according to claim 1, wherein a plurality of protrusions is formed on the frame surface of the button protective cap so that the worker can easily find and operate the grinding mode selector switch for welding masks by hand.

4. The grinding mode selector switch for welding masks according to claim 1, wherein a sub-button protective cap including a through hole formed at a center thereof so as to be detachably attached to an upper portion of the button protective cap and a joining projection formed on a side surface thereof is provided.

5. The grinding mode selector switch for welding masks according to claim 1, wherein a fluorescent material is applied to the button protective cap or the button.

* * * * *